(12) United States Patent
Wang et al.

(10) Patent No.: US 8,090,431 B2
(45) Date of Patent: Jan. 3, 2012

(54) SYSTEMS AND METHODS FOR BIOLUMINESCENT COMPUTED TOMOGRAPHIC RECONSTRUCTION

(75) Inventors: Ge Wang, Iowa City, IA (US); Eric Hoffman, Iowa City, IA (US); Geoffrey McLennan, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 1029 days.

(21) Appl. No.: 10/791,140

(22) Filed: Mar. 2, 2004

(65) Prior Publication Data

US 2004/0249260 A1  Dec. 9, 2004

Related U.S. Application Data

(60) Provisional application No. 60/453,177, filed on Mar. 10, 2003.

(51) Int. Cl.
*A61B 6/00* (2006.01)
(52) U.S. Cl. .................... 600/473; 600/425; 600/476
(58) Field of Classification Search ............ 356/72, 356/73; 600/310, 317, 407, 425, 473, 476
See application file for complete search history.

(56) References Cited

U.S. PATENT DOCUMENTS

| 4,611,600 | A | 9/1986 | Cohen |
| 5,202,091 | A | 4/1993 | Lisenbee |
| 5,350,377 | A | 9/1994 | Winston et al. |
| 5,608,221 | A | 3/1997 | Bertelsen et al. |
| 6,002,743 | A | 12/1999 | Telymonde |
| 6,216,027 | B1 | 4/2001 | Willis et al. |
| 6,217,847 | B1 | 4/2001 | Contag et al. |
| 6,333,960 | B1 | 12/2001 | Tam |
| 6,429,434 | B1 | 8/2002 | Watson et al. |
| 6,463,118 | B2 | 10/2002 | Besson |
| 6,490,476 | B1* | 12/2002 | Townsend et al. ............ 600/427 |
| 6,631,284 | B2* | 10/2003 | Nutt et al. .................... 600/427 |
| 6,801,595 | B2* | 10/2004 | Grodzins et al. ............... 378/45 |

(Continued)

FOREIGN PATENT DOCUMENTS

WO  WO 01/63247 A2  2/2001

(Continued)

OTHER PUBLICATIONS

Warren et al., "Combined Ultrasound and Fluorescence Spectroscopy for Physico-Chemical Imaging of Atherosclerosis". IEEE Transactions on Biomedical Engineering 42(2) (1995): 121-132.*

(Continued)

*Primary Examiner* — Tse Chen
*Assistant Examiner* — Peter Luong
(74) *Attorney, Agent, or Firm* — Ballard Spahr LLP

(57) ABSTRACT

An image of an object is synergistically reconstructed using two or multiple imaging modalities. A first reconstructed image, showing structural information of the object is produced using a first imaging modality. The first reconstructed image is segmented, and known optical properties of the object are then mapped to the first reconstructed image. Optical signal emissions from the object are detected and registered with the first reconstructed image. A second reconstructed image volume is then produced using a second imaging modality, based on the mapped optical properties after registration between the first image and the data from the second modality. The second reconstructed image depicts some optical property, such as a bioluminescent source distribution, or optical properties, such as, attenuation and scattering properties, of the object.

27 Claims, 4 Drawing Sheets

U.S. PATENT DOCUMENTS

| | | | |
|---|---|---|---|
| 7,190,991 B2* | 3/2007 | Cable et al. | 600/407 |
| 7,251,523 B2* | 7/2007 | Kojima et al. | 600/427 |
| 2002/0077543 A1 | 6/2002 | Grzeszczuk et al. | |
| 2003/0087244 A1* | 5/2003 | McCarthy | 435/6 |
| 2003/0120150 A1 | 6/2003 | Govari | |
| 2003/0191398 A1 | 10/2003 | Motz et al. | |
| 2004/0015062 A1 | 1/2004 | Ntziachristos et al. | |
| 2004/0021771 A1 | 2/2004 | Stearns et al. | |
| 2004/0092829 A1 | 5/2004 | Furnish et al. | |
| 2004/0215072 A1* | 10/2004 | Zhu | 600/407 |
| 2005/0149877 A1 | 7/2005 | Rice et al. | |
| 2005/0201614 A1 | 9/2005 | Rice et al. | |
| 2007/0093700 A1 | 4/2007 | Wang et al. | |

FOREIGN PATENT DOCUMENTS

| | | |
|---|---|---|
| WO | WO-2004/081865 A2 | 9/2004 |

OTHER PUBLICATIONS

Peter et al., "Design Study of a Novel Dual-Modality Emission Micro-Imaging Tomograph for Radiopharmaceutical and Bioluminescent/Fluorescent Molecular Approaches". IEEE Int'l Symp. on Biomedical Imaging Proceedings (2002): 797-800.*
"Tomography—Definition from Dictionary.com". Aug. 11, 2008.*
"Bioluminescent Indicators in Living Mammals," Contag et al., published in Nature Medicine, New Technology Section (1998) 4(2): 245-247.
"Visualizing Gene Expression in Living Mammals Using a Bioluminescent Reporter," Contag et al., published in Photochemistry and Photobiology (1997) 66(4):523-531.
Zitova, et al.; Image Registration Methods: A Survey; 24 pgs; Image and Vision Computing 21 (2003) 977-1000.
Amirav, I., Kramer, S. S., Grunstein, M. M., and E.A. Hoffman, "Assessment of methacholine-induced airway constriction by high resolution cine computed tomography (HRCCT)," J. Applied Physiology, 1993, pp. 2239-2250, vol. 75(5).
J. Beuthan, et al., "Optical molecular imaging: Overview and technological aspects," Med. Laser Appl., 2002, pp. 25-30, vol. 17.
S. Bhaumik, and S. S. Gambhir, "Optical imaging of *Renilla luciferase* reporter gene expression in living mice," Proc. Natl. Acad. Sci., 2002, pp. 377-382, vol. 99(1), USA.
D. A. Boas, "Diffuse Photon Probes of Structural and Dynamical Properties of Turbid Media: Theory and Biomedical Applications," 1996, Massachusetts General Hospital, Charlestown, MA, Harvard University.
D. A. Boas, et al., "The accuracy of near infrared spectroscopy and imaging during focal changes in cerebral hemodynamics," Neuroimage, 2001, pp. 76-90, vol. 13(1).
C. Bremer, et al., "Optical-based molecular imaging: contrast agents and potential medical applications," Eur. Radiol., 2003, pp. 231-243, vol. 13.
I. Bronstein, et al., "Chemiluminescent and bioluminescent reporter gene assays," Analytical. Biochemistry., 1994, pp. 169-181, vol. 219(2).
T. F. Budinger, T. F., D. A. Benaron, et al., "Imaging transgenic animals," Annu. Rev. Biomed. Eng., 1999, pp. 611-648, vol. 1.
W.-F. Cheong, et al., "A review of the optical properties of biological tissues," IEEE Journal of Quantum Electronics, 1990, pp. 2166-2185, vol. 26.
C. H. Contag, et al., "Use of reporter genes for optical measurements of neoplastic disease in vivo," Neoplasia, 2000, pp. 41-52, vol. 2(1-2).
C. H. Contag, et al., "Advances in in vivo bioluminescence imaging of gene expression," Annual. Rev. Biomed. Eng., 2000, pp. 235-260, vol. 4.
S. M. Graham, et al., "Preoperative assessment of obstruction with computed tomography image analysis," Am. J. Otolaryngol., 2000, pp. 263-270, vol. 21(4).
J. Hardy, et al., "Bioluminescence imaging of lymphocyte trafficking in vivo," Experimental. Hematology, 2001, pp. 1353-1360, vol. 129(12).
R. C. Haskell, et al., "Boundary conditions for the diffusion equation in radiative transfer," J. Opt. Soc. Am. A, 1994, pp. 2727-2741, vol. 11(10).
J. W. Hastings, "Chemistries and colors of bioluminescent reactions: a review," Gene., 1996, pp. 5-11, vol. 73.
M. Jiang and G. Wang, "Convergence Studies on Iterative algorithms for image reconstruction," IEEE Trans. on Medical Imaging, 2002, pp. 569-579, vol. 22(5).
M. Jiang and G. Wang, "Development of Iterative Algorithms for Image Reconstruction," Journal of X-Ray Science and Technology, 2002, pp. 77-86, vol. 10.
A. D. Kim et al., "Light propagation in biological tissue," J. Opt. Soc. Am. A, 2003, pp. 92-98, vol. 20(1).
W. F. Kolbe and B. T. Turko, "Recovery of very low intensity CCD images from noise," IEEE Trans. Nuclear Science, 1989, pp. 731-733, vol. 36(1).
Liu, Y., H. Liu, et al., "Half-scan cone-beam CT fluoroscopy with multiple x-ray sources," Med. Phys., 2001, pp. 1466-1471, vol. 28(7).
V. Ntziachristos, et al., "Fluorescence molecular tomography resolves protease activity in vivo," Nature Medicine, 2002, pp. 757-760, vol. 8(7).
V. Ntziachristos, et al. "Concurrent MRI and diffuse optical tomography of breast aRer indocyanine green enhancement," Proc. Natl. Acad. Sci. U.S.A., 2000, pp. 2767-2772, vol. 97(6).
V. Ntziachristos, et al., "Diffuse optical tomography of highly heterogeneous media," IEEE Trans. Med. Imaging, 2001, pp. 470-478, vol. 20(6).
M. O'Leary, "Imaging with Diffuse Photon Density Waves," 1996. Massachusetts General Hospital. Charlestown, MA, Harvard University.
B. W. Pogue, et al., "Initial assessment of a simple system for frequency domain diffuse optical tomography," Phys. Med. Biol., 1995, pp. 1709-1729, vol. 140(10).
Rehemtulla, et al., "Rapid and quantitative assessment of cancer treatment response using in vivo bioluminescence imaging," Neoplasia, 2000, pp. 491-495, vol. 2(6).
W. Rice, et al., "In vivo imaging of light-emitting probes," J. Biomed. Opt., 2001, pp. 432-440, vol. 6(4).
L. A. Shepp and Y. Vardi, "Maximum likelihood restoration for emission tomography," IEEE Trans. Med. Imaging, 1982, pp. 113-122, vol. 1.
J. Tanifuji and M. Hijikata., "Finite difference time domain (FDTD) analysis of optical pulse responses in biological tissues for spectroscopic diffused optical tomography," IEEE Trans. Med. Imaging, 2002, pp. 181-184, vol. 21(2).
U. Utzinger, et al., "Fiber optic probes for biomedical optical spectroscopy," Journal of Biomedical Optics, 2003, pp. 121-147, vol. 8(1).
G. Wang and P. C. Cheng, "Feldkamp-type cone-beam reconstruction: Revisited," Zoological Studies, 1995, pp. 159-161, vol. 34(S).
G. Wang, et al., "Guest editorial: Multi-row-detector and cone-beam spiral/helical CT" IEEE Trans. Medical Imaging, 2000, pp. 817-821, vol. 19.
G. Wang and M. W. Vannier, et al., "Fast iterative algorithm for metal artifact reduction in X-ray CT,". Acad. Radiol., 2000, pp. 607-614, vol. 7.
G. Wang, et al., "Error analysis on the generalized Feldkamp cone-beam computed tomography algorithm," Scanning, 1995, pp. 361-370, vol. 17.
Wang G., et al., "A Study on the section sensitivity profile in multi-row-detector spiral CT," Journal of X-Ray Science and Technology, 2003, pp. 1-11, vol. 11.
G. Wang, et al., "An iterative algorithm for X-ray CT fluoroscopy," IEEE Transactions on Medical Imaging, 1998, pp. 853-856, vol. 17.
G. Wang, et al., "Temporal bone volumetric image deblurring in spiral CT," Academic Radiology 1995, pp. 888-895, vol. 2.
Wang G., et al., "Iterative deblurring for CT metal artifact reduction," IEEE Trans. on Medical Imaging, 1996, pp. 657-664, vol. 15.
G. Wang, et al., "Local computed tomography via iterative deblurring," Scanning, 1996, pp. 582-588, vol. 18.
Wang G., Vannier M. W., "Micro-CT scanners for biomedical applications: an overview," Advanced Imaging, 2001, pp. 18,22-27, vol. 16., www.advancedimagingmag.com.

G. Wang, et al. "Cone-beam X-ray tomographic and stereo-imaging," Biomedical Engineering-Applications, Basis & Communications, 1996, pp. 261-271, vol. 8.

Wang, G., Lin TH, et al., "A general cone-beam reconstruction algorithm," IEEE Trans. on Medical Imaging, 1993, pp. 486-496, vol. 13.

S. Wood, et al., "Measurement of Three-Dimensional Lung Tree Structures Using Computed Tomography,". J. Appl. Physiol., 1995, pp. 1687-1697, vol. 79(5).

S. Zhao and G. Wang, "Feldkamp-type cone-beam tomography in the wavelet framework," IEEE Trans. Med. Imaging, 2000, pp. 922-929, vol. 19(9).

C. H. Contag et al., "It's not just about anatomy: in vivo bioluminescence imaging as an eyepiece into biology." J. Magn. Reson. Imaging, 2002, pp. 378-387, vol. 16(4).

P. R. Contag et al., "Whole-animal cellular and molecular imaging to accelerate drug development," Drug Discovery. Today, 2002, pp. 555-562, vol. 7(10).

M. Defrise, et al., "A solution to the long-object problem in helical cone-beam tomography," Phys. Med. Biol., 2000, pp. 623-643, vol. 45(3).

Farkas, et al., "Applications of spectral imaging: Detection and analysis of human melanoma and its precursors," Pigment Cell. Res., 2001, pp. 2-8, vol. 14(1).

P. Grenier, et al. "High-resolution computed tomography of the airways." J. Thoracic Imag., 1993, pp. 213-229, vol. 8(3).

A. H. Hielscher et al., "Near-infrared diffuse optical tomography," Disease. Markers, 2002, pp. 313-337, vol. 18(5-6).

Hoffman, E. A., et al., "VIDA: An environment for multidimensional image display and analysis," SPIE Biomedical Image Processing and Three-Dimensional Microscopy, San Jose, CA. Bellingham, WA, SPIE, 1992, pp. 694-711, vol. 1660.

M. J. Holboke, et al., "Three-dimensional diffuse optical mammography with ultrasound localization in a human subject," J. Biomed. Opt., 2000, pp. 237-247, vol. 5(2).

B. Li, et al., "3-D inter-subject warping and registration of pulmonary CT images for a human lung model," Proc. SPIE Medical Imaging 2002: Physiology and Function from Multidimensional Images, San Diego, CA., 2002, pp. 324-335, vol. 4683.

M. Reinhardt and E. A. Hoffman, "Quantitative pulmonary imaging: Spatial and temporal considerations in HRCT," Acad. Radiol., 1998, pp. 539-546, vol. 5(8).

B. D. Ross et al., "Magnetic resonance imaging in cancer research," European Journal. Of Cancer, 2002, pp. 2147-2156, vol. 38(16).

A. J. Sherbondy, et al., "Virtual Bronchoscopy Approach for Combining 3D CT and Endoscopic Video," SPIE Medical Imaging 2000: Physiology and Function from Multidimensional Images, 2000, pp. 104-116, vol. 3978.

Tajik et al, "Subsecond multisection CT of regional pulmonary ventilation," Acad. Radiol., 2002, pp. 130-146, vol. 9(2).

G. Wang, et al., "Scanning cone-beam reconstruction algorithms for x-ray microtomography," Proc. SPIE Scanning Microscopy Intrumentation, 1991, pp. 99-112, vol. 1556.

G. Wang, et al., "Cone-beam reconstruction for micro-CT," The 2002 IEEE International Symposium on Biomedical Imaging, Washington DC, 2002, pp. 384-387.

Zhang and J. Reinhardt, "Detection of Lung Lobar Fissures using Fuzzy Logic," Medical Imaging 1999: Physiology and function from multidimensional images, San Diego, CA, Proc. SPIE, 1999, pp. 188-199, vol. 3660.

Amendment entered with Filing of RCE filed Dec. 22, 2010 for U.S. Appl. No. 11/444,282, filed May 31, 2006 (Inventors:—Wang et al.).

Final Rejection issued Sep. 28, 2010 for U.S. Appl. No. 11/444,282, filed May 31, 2006 (Inventors:—Wang et al.).

Response to Non-Final Action filed Mar. 25, 2010 for U.S. Appl. No. 11/444,282, filed May 31, 2006 (Inventors:—Wang et al.).

Non-Final Rejection issued Oct. 26, 2009 for U.S. Appl. No. 11/444,282, filed May 31, 2006 (Inventors:—Wang et al.).

Response to Election/Restriction filed Jul. 29, 2009 for U.S. Appl. No. 11/444,282, filed May 31, 2006 (Inventors: Wang et al.).

Requirement for Restriction/Election issued Mar. 18, 2009 for U.S. Appl. No. 11/444,282, filed May 31, 2006 (Inventors:—Wang et al.).

International Preliminary Report on Patentability issued Sep. 16, 2005 for Intl. App. No. PCT/US04/006360, filed Mar. 2, 2004 (Applicant—University of Iowa Research Foundation; Inventors: Wang et al).

International Search Report issued May 20, 2005 in Intl. App. No. PCT/US04/006360, filed Mar. 2, 2004 (Applicant: University of Iowa Research Foundation; Inventors: Wang et al).

Written Opinion issued May 20, 2005 in Intl. App. No. PCT/US04/006360, filed Mar. 2, 2004 (Applicant: University of Iowa Research Foundation; Inventors: Wang et al).

Andersen, A. H. and Kak A. C., "Simultaneous algebraic reconstruction technique (SART): a superior implementation of the ART algorithm," Ultrason. Imaging, 1984, pp. 81-94, vol. 6. (Only abstract is enclosed).

Blouke, M. M., et al., "Large area CCD image sensors for scientific applications," Proc S.P.I.E Conf., 1985, pp. 82-88. (Only abstract is enclosed).

Browne, J. and de Pierro A. B., "A row-action alternative to the EM algorithm for maximizing likelihoods in emission tomography," IEEE Trans. on Med. Imaging, 1996, pp. 687-699, vol. 15.

Dennis, J. B., "Non-linear least squares and equations," The state of the art in numerical analysis: proceedings of the Conference on the State of the Art in Numerical Analysis, D. A. H. Jacobs (Ed.), Academic Press: London, 1977, pp. 269-312.

Everhart, J., et al., "Image segmentation applied to CT examination of lymphangioleiomyomatosis (LAM)," Proc. SPIE Conf. Med. Imaging, Newport Beach, CA., 1994, pp. 87-95, vol. 2167.

Francis, K. P., et al., "Monitoring bioluminescent *Staphylococcus aureus* infections in living mice using a novel luxABCDE construct," Infect. Immure., 2000, pp. 3594-3600, vol. 68.

Gaudette, R., "Constrained Reconstruction Techniques for Diffuse Optical Tomography," Massachusetts General Hospital. Charlestown, MA, Harvard University, 2000.

Hoffman, E. A. and Ritman E. L., "Constancy of total heart volume throughout cardiac cycle and role of lung inflation: A computer tomographic measurement with DSR," Federation Proceedings, 1994, pp. 509, vol. 43(3).

Hoffman, E. A. and Ritman E. L., "Effect of body orientation on regional lung expansion in dog and sloth," J. Appl. Physiol., 1985, pp. 481-491, vol. 59(2).

Hoffman, E. A. and Hoford J. D., "Tool box-based cardiac volumes: Visualization and quantitation by computed tomography," Am. J. Card. Imaging, 1993, pp. 164-178, vol. 7. (Only abstract is enclosed).

Hoffman, E. A., et al., "Regional pleural surface expansile forces in intact dogs by wick catheters," J. Appl. Physiol., 1983, pp. 1523-1519, vol. 55(5).

Hoffman, E. A. and Ritman E. L., "Shape and dimensions of cardiac chambers: Importance of CT section thickness and orientation," Radiol., 1985, pp. 739-744, vol. 155(3).

Hoffman, E. A. and McLennan G., "Assessment of the pulmonary structure-function relationship and clinical outcomes measures: Quantitative volumetric CT of the lung," Acad. Radiol., 1997, pp. 758-776, vol. 4.

Hoffman, E. A., et al., "Matching Pulmonary Structure and Perfusion via Combined Dynamic Multislice CT and Thin-Slice High Resolution CT," Comput. Med. Imaging Graph., 1995, pp. 101-112, vol. 19(1).

Hoffman, E. A., et al., "Noninvasive quantitative imaging of shape and volume of lungs," J. Appl. Physiol.: Respirat. Environ. Exercise Physiol., 1983, pp. 1414-1421, vol. 54(5).

Hoffman, E. A., "Effect of body orientation on regional lung expansion: A computed tomographic approach," J. Appl. Physiol., 1985, pp. 468-480, vol. 59(2).

Hudson, H. M. and Larkin R. S., "Accelerated image reconstruction using ordered subsets of projection data," IEEE Trans. on Med. Imaging, 1994, pp. 601-609, vol. 13.

Iwasaki, T., et al., "Mass of left ventricular myocardium estimated with dynamic spatial reconstructor," Am. J. Physiol., 1984, pp. 1138-1142, vol. 246(1 Pt 2).

Jiang, M. and Wang G., "Block-Iterative Algorithms for Image Reconstruction," Mathematical Software, Proceedings of the First International Congress of Mathematical Software, Beijing, China, World Scientific, 2002, pp. 51-60.

Joyeaux, A., et al., "Engineered cell lines as a tool for monitoring biological activity of hormone analogs," Anal. Biochem., 1997, pp. 119-130, vol. 249.

Liu, Y., et al., "Accuracy of pulmonary vascular dimensions estimated with the Dynamic Spatial Reconstructor," Am. J. Physiol. Imaging, 1986, pp. 201-207, vol. 1. (Only abstract is enclosed).

Liu, Y., et al., "Measurement of Three-Dimensional anatomy and Function of pulmonary arteries with high-speed x-ray computed tomography," Invest. Radiol., 1987, pp. 28-36, vol. 22.

Margulies, S. S., et al., "Geometry and Kinematics of Dog Ribs," J. Appl. Physiol., 1989, pp. 707-712, vol. 67(2).

McNamara, A. E., et al., "Airway narrowing in excised canine lungs measured by high-resolution computed tomography," J. Appl. Physiol., 1992, pp. 307-316, vol. 73(1).

Olson, L. E. and Hoffman E. A., "Heart-lung interactions determined by electron beam X-ray CT in laterally recumbent rabbits," J. Appl. Physiol., 1995, pp. 417-427, vol. 78(2).

Olson, L. E. and Hoffman E. A., "Lung Volumes and Distribution of Regional Air Content Determined by Cine X-ray CT of Pneumonectomized Rabbits," J. Appl. Physiol., 1994, pp. 1774-1785, vol. 76(4).

Park, W., et al., "Segmentation of Intrathoracic Airway Trees: A Fuzzy Logic Approach," IEEE Trans. on Med. Imaging, 1998, pp. 489-497, vol. 17.

Ray, P., et al., "Optical bioluminescence and positron emission tomography imaging of a novel fusion reporter gene in tumor xenografts of living mice," Cancer Res., 2003, pp. 1160-1165, vol. 63(6).

Reinhardt, J. M., et al., "Accurate measurement of intra-thoracic airways," IEEE Trans. on Med. Imaging, 1997, pp. 820-827, vol. 16(6).

Robb, R. A., et al., "High-speed three-dimensional, x-ray Computed Tomography: The Dynamic Spatial Reconstructor" Proceed. of the IEEE, 1983, pp. 308-319, vol. 71(3).

Schaller, S., et al., "An efficient Fourier method for 3-D radon inversion in exact cone-beam CT reconstruction," IEEE Trans. Med. Imaging, 1998, pp. 244-250, vol. 17(2).

Schwab, R. J., et al., "Dynamic imaging of the upper airway during respiration in normal subjects," J. Appl. Physiol., 1993, pp. 1504-1514, vol. 74(4).

Sinak, L. J., et al., "Subtraction gated computed tomography with the dynamic spatial reconstructor: simultaneous evaluation of left and right heart from single right-sided bolus contrast medium injection," J. Comput. Assist. Tomogr., 1984, pp. 1-9, vol. 8(1).

Smith, J. J., et al. "Cystic fibrosis airway epithelia fail to kill bacteria because of abnormal airway surface fluid," Cell., 1996, pp. 229-236, vol. 85.

Snyder, D. L., et al., "Deblurring subject to nonnegativity constraints," IEEE Trans. on Signal Processing, 1992, pp. 1143-1150, vol. 40.

Sonka, M., et al., "Knowledge-Based Segmentation of Intrathoracic Airways from Multidimensional High Resolution CT Images," SPIE Physiology and Function from Multidimensional Images, 1994, pp. 73-85, vol. 2168.

Sonka, M., et al., "Rule-Based Detection of Intrathoracic Airway Trees," IEEE Trans. on Med. Imaging, 1996, pp. 314-326, vol. 15(3).

Travis, S. M., et al., "Activity of abundant antimicrobials of the human airway," Am. J. Respir. Cell. Mol. Biol., 1999, pp. 872-879, vol. 20.

Uppaluri, R., et al., "Computer recognition of regional lung disease patterns," Am. J. Respir. Crit. Care Med.,1999, pp. 648-654, vol. 160(2).

Uppaluri, R., et al., "Quantification of Pulmonary Emphysema from Lung Computed Tomography Images," Am. J. Respir. Crit. Care Med., 1997, pp. 248-254, vol. 156(1).

Wang, G., et al., "Theoretical FWTM values in helical CT," Med. Phys., 1994, pp. 753-754, vol. 21.

Wang, G., et al., "Digital X-ray stereophotogrammetry for cochlear implantation," IEEE Trans. on Biomedical Engineering, 2000, pp. 1120-1130, vol. 47.

Wang, G. and Vannier M. W., "Helical CT image noise—Analytical results," Med. Phys., 1993, pp. 1635-1640, vol. 20.

Wang, G. and Vannier M. W., "Longitudinal resolution in volumetric X-ray computed tomography—Analytical comparison between conventional and helical computed tomography," Med. Phys., 1994, pp. 429-433, vol. 21.

Wang, G. and Vannier M. W., "Low-contrast resolution in volumetric X-ray CT—Analytical comparison between conventional and spiral CT," Med. Phys., 1997, pp. 373-376, vol. 24.

Wang, G. and Vannier M. W., "Maximum volume coverage in spiral computed tomography," Acad. Radiol., 1996, pp. 423-428, vol. 3.

Wang, G. and Vannier M. W., "Optimal pitch in spiral computed tomography," Med. Phys., 1997, pp. 1635-1639, vol. 24.

Wang, G. and Vannier M. W., "Preliminary Study on helical CT algorithms for patient motion estimation and compensation," IEEE Trans. on Med. Imaging, 1995, pp. 205-211, vol. 14.

Wang, G. and Vannier M. W., "Spatial variation of section sensitivity profile in spinal computed tomography," Med. Phys., 1994, pp. 1491-1497, vol. 21.

Wang, G. and Vannier M. W., "Stair-step artifacts in three-dimensional helical CT: An experimental study," Radiol., 1994, pp. 79-83, vol. 191.

Wang, G., et al., "Iterative X-ray cone-beam tomography for metal artifact reduction and local region reconstruction," Microscopy and Microanalysis, 1999, pp. 58-65, vol. 5.

Wang, G., et al., "Spiral CT image deblurring for cochlear implantation," IEEE Trans. on Med. Imag., 1998, pp. 251-262, vol. 17.

Wang, G., et al., "Unwrapping cochlear implants by spiral CT," IEEE Trans. on Biomedical Engineering, 1996, pp. 891-900, vol. 43.

Wang, G. and Vannier M. W., "The effect of pitch in multislice spiral/helical CT," Med. Phys., 1999, pp. 2648-2653, vol. 26.

Wang, G., et al, "Development of retroviral vectors for gene transfer to airway epithelia," Curr. Opin. Mol. Ther., 2000, pp. 497-506, vol. 2(5).

Wang, G., et al., "A knowledge-based cone-beam X-ray CT algorithm for dynamic volumetric cardiac imaging," Med. Phys., 2002, pp. 1807-1822, vol. 29(8).

Wang, G., et al., "An iterative algorithm for X-ray CT fluoroscopy," IEEE Trans. Med. Imaging, 1998, pp. 853-856, vol. 17(5).

Wang, G., et al., "A derivative-free noncircular fan-beam reconstruction formula," IEEE Trans. on Image Processing, 1993, pp. 543-547, vol. 2.

Wang, G., et al., "Cone-beam reconstruction of plate-like specimens," Scanning, 1992, pp. 350-354, vol. 14.

Wang, G., et al., "Point spread function of the general cone-beam X-ray reconstruction formula," Scanning, 1992, pp. 187-193, vol. 14.

Wang, G., et al., "Feline immunodeficiency virus vectors persistently transduce nondividing airway epithelia and correct the cystic fibrosis defect," J. Clin. Invest., 1999, pp. R49-R56, vol. 104.

Wang, G. and Han W., "Minimum error bound of signal reconstruction," IEEE Signal Processing Letters, 1999, pp. 309-311, vol. 6.

Wang, G. and Li Y., "Axiomatic approach for quantification of image resolution," IEEE Signal Processing Letters, 1999, pp. 257-258, vol. 6.

Wang, G., et al., "Half-scan cone-beam X-ray microtomography formula," Scanning, 1994, pp. 216-220, vol. 16.

Wang, G., "X-ray micro-CT with a displaced detector array," Med. Phys., 2002, pp. 1634-1636, vol. 29.

Wei, J. H., et al., "Cardiogenic motion of right lung parenchyma in anesthetized intact dogs," J. Appl. Physiol., 1985, pp. 384-391, vol. 58(2).

Welsh, M. J., et al., "Cystic Fibrosis," The Metabolic and Molecular Basis of Inherited Disease, C. R. Scriver, A. L. Beaudet, W. S. Sly and D. Valle (eds.), New York, McGraw-Hill, 1995, pp. 3799-3855, vol. 3.

Welsh, S. and Kay S. A., "Reporter gene expression for monitoring gene transfer," Curr. Opin. Biotechnol., 1997, pp. 617-622, vol. 8.

Wilson, T. A., et al., "Geometry and respiratory displacement of human ribs, " J. Appl. Physiol., 1987, pp. 1872-1877, vol. 62.

Jiang, M. and Wang G., "Convergence of the Simultaneous Algebraic Reconstruction Technique (SART)," IEEE Trans. Image Process., 2003, pp. 957-961, vol. 12(8).

Jiang, M., et al., "Blind deblurring for spiral CT images," IEEE Trans. Med. Imaging, 2003, pp. 837-845, vol. 22(7).

Grangeat, P., "Mathematical framework of cone beam 3D reconstruction via the first derivative of the Radon transform," Mathematical Methods in Tomography, Lecture notes in Mathematics, Proceedings, Oberwolfach 1990, Springer-Verlag, 1991, pp. 66-94.

\* cited by examiner

Pulmonary Bioluminescence:
Visible from Multiple Angles of View

SYSTEMS AND METHODS FOR BIOLUMINESCENT COMPUTED TOMOGRAPHIC RECONSTRUCTION

CROSS-REFERENCE TO RELATED APPLICATION

This application claims priority to U.S. Provisional Application No. 60/453,177 filed Mar. 10, 2003 and hereby incorporated by reference.

BACKGROUND

This invention relates to multi-modality-based systems and methods for detecting an optical property distribution, such as a light-emitting source distribution, in multiple dimensions as well as systems and methods for reconstructing such an image from the detected signals from the distribution based on data from a tomographic imaging modality, including but not limited to computed tomography (CT) or micro-CT.

There are many "emission-detection" imaging techniques known in the art, such as bioluminescent imaging. However, such current imaging techniques are limited to the projective imaging mode or external excitation of the internal light source through external energy sources along selected paths. Therefore, three-dimensional structures and localization of an internally derived light source, such as one not reliant on external energy excitation, cannot be resolved with high quantitative accuracy both in terms of spatial location and localized activity.

Diffuse computed tomography (CT), another known imaging technique, computes distributions of absorption and scattering coefficients from scattered light through an object. Typically, intensity-modulated light sources are used. It is well known that diffuse CT will generally produce low image resolution, particularly as background heterogeneity increases.

It would therefore be desirable to combine an optical imaging technique, such as a light emission technique, specifically bioluminescent imaging, with a scanning technique that allows the evaluation of two and three dimensional structural information, such as computed tomography scanning or magnetic resonance imaging, to produce a reconstructed image having better image resolution.

SUMMARY

The present invention is directed to multi-modal imaging systems and methods that reconstruct images via fundamental and synergistic utilization of multi-model data. According to an exemplary embodiment, an image volume may be reconstructed in a first tomographic modality, optical properties from a database may be mapped to the image volume, and the image may then be reconstructed tomographically in another modality, based on the optical properties.

According to one embodiment, bioluminescent CT and CT/micro-CT combinations may be used, but other system configurations are possible. Some embodiments may include a magnetic resonance imaging (MRI) scanner or micro-MRI scanner in conjunction with a fluorescent tomographic scanner. The imaging techniques and algorithms described herein are exemplary only, and other methods of combining data from two or more tomographic scanners may be used.

Some embodiments may be capable of various resolutions depending on scanning times, possess extremely high photon detection sensitivity for mapping gene expression, and/or embody hardware and/or software technology for image reconstruction, registration, and analysis. Some embodiments may have the advantage of being configured to rapidly collect data with a higher signal-to-noise ratio.

According to one embodiment, bioluminescent imaging may be rendered in a two- or three-dimensional tomographic modality. In embodiments directed to bioluminescence, emitted photons can be collected from multiple three-dimensional directions with respect to an animal marked by bioluminescent compounds including reporter luciferases.

According to some embodiments, a CT or micro-CT scanner may be integrated with a bioluminescent imaging system. The bioluminescent imaging system may also be combined with other imaging systems which provide information regarding the distribution of tissue structures in vivo, in situ, or ex vivo.

In alternative embodiments, an object may be serially scanned using each modality in turn. In still further embodiments, the object may be transported between scanning modalities. Optionally, one or more registration marks may be placed on the object to coordinate positions between scanning modalities. The surface of the object may also be optically reconstructed for the registration purpose.

In some embodiments, information associated with x-ray CT imaging and bioluminescent imaging may be used together to estimate light scatter and/or other optical properties of tissue and thereby reconstruct a three-dimensional emission image volume registered to corresponding CT or micro-CT imaging of anatomical and pathological structures. As non-limiting examples, the system may be used to generate images of structures, such as bioluminescent sources, lungs and various tumors.

According to some embodiments, intra-organ localization of gene transcription activity may be performed with resolution capable of differentiating, for instance, gene expression in the central pulmonary airways (out to approximately the 5th-7th generation) versus parenchymal activity. Also, localization of parenchymal activity in terms of sub-lobar regions may be performed. As a non-limiting example, small animal imaging, in particular mouse imaging, may be performed. In other examples, the systems and methods may be used for other biomedical applications where bioluminescent signals are detectable. Some embodiments are especially suited for small animal imaging at molecular levels. For example, genetic activity in a particular organ system may be imaged.

By integrating x-ray and optical imaging, better optical tomography image quality can be achieved that would not be possible with a stand-alone optical system. From a corresponding x-ray CT image volume or image volume generated by other imaging energy sources, knowledge of the underlying distribution of optical scatters can be derived. This information is useful in reconstruction of images from optical data. Specifically, emitting source distributions may be directly solved for, obviating the need for reconstruction of optical properties in three dimensions.

According to exemplary embodiments, the combined use of x-ray CT and BLCT transforms the nonlinear optical CT problem into an easier linear problem. Therefore, the reconstruction of image data from a bioluminescent CT scanner may be significantly improved.

One embodiment includes a system processor that supports the desired functionality as described in detail below and a system data store (SDS) that stores data associated with the needed functionalities, such as image data and reconstruction. The system processor may be in communication with the SDS via any suitable communication channel(s).

The SDS may include multiple physical and/or logical data stores for storing the various types of information used. Data storage and retrieval functionality can be provided by either the system processor or one or more data storage processors associated with the SDS. The system processor may include one or more processing elements that are adapted or programmed to support the desired image storage, reconstruction and/or other functionality.

Accordingly, one method of image reconstruction includes a variety of steps that may, in certain embodiments, be executed by the environment summarized above and more fully described below or be stored as computer executable instructions in and/or on any suitable combination of computer-readable media. The steps can include but are not limited to performing tomographic reconstruction of an image volume in one modality, mapping optical properties to that volume from a database, and performing tomographic reconstruction in another modality based on the mapped optical properties.

Additional advantages of the invention will be set forth in part in the description which follows, and in part will be obvious from the description, or may be learned by practice of the invention. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

DETAILED DESCRIPTION

Figure 1:
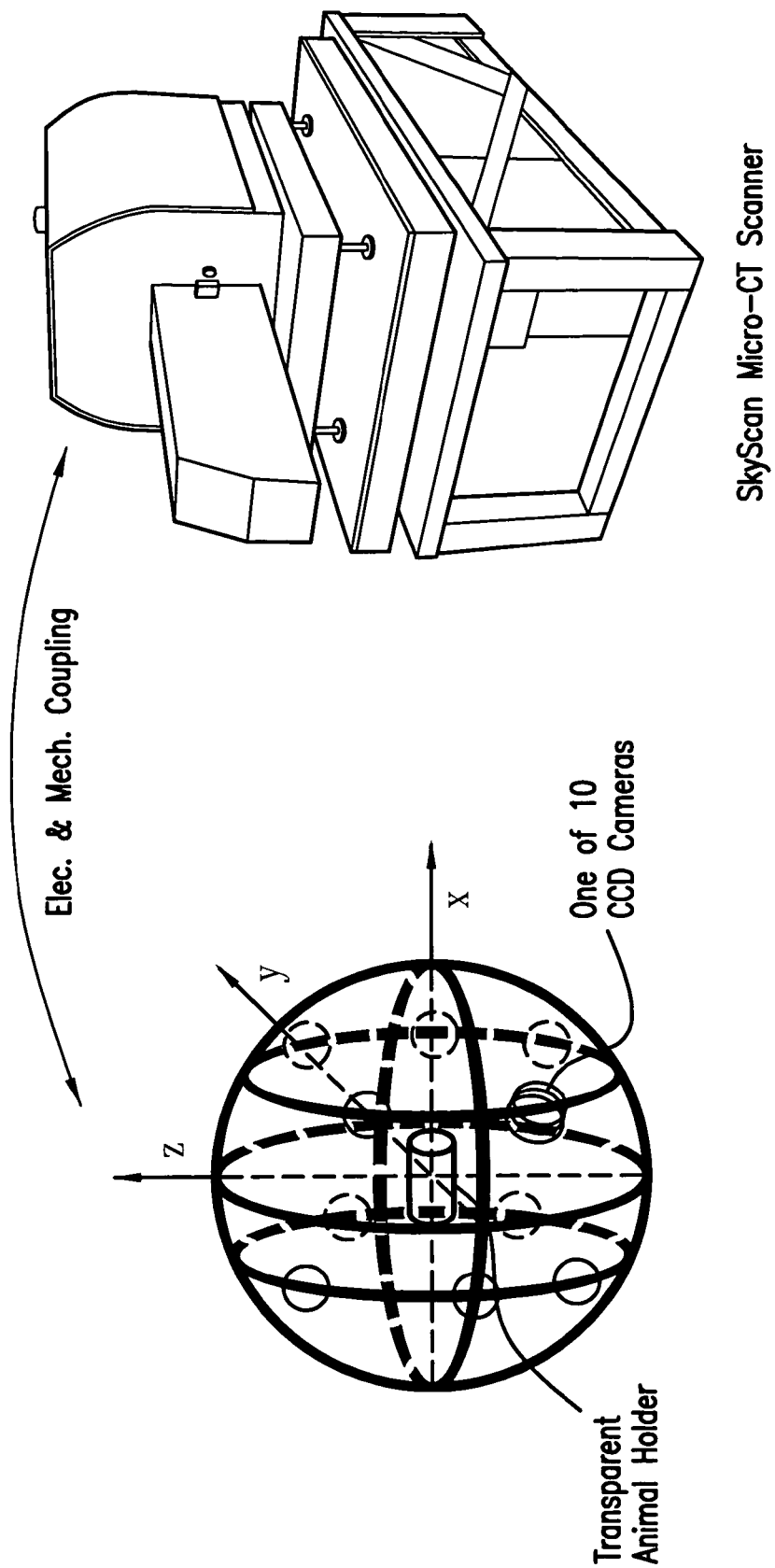
FIG. 1 depicts an exemplary bioluminescent imaging device (left panel) with an anatomic imaging device (micro CT scanner shown in the right panel).
Figure 2:
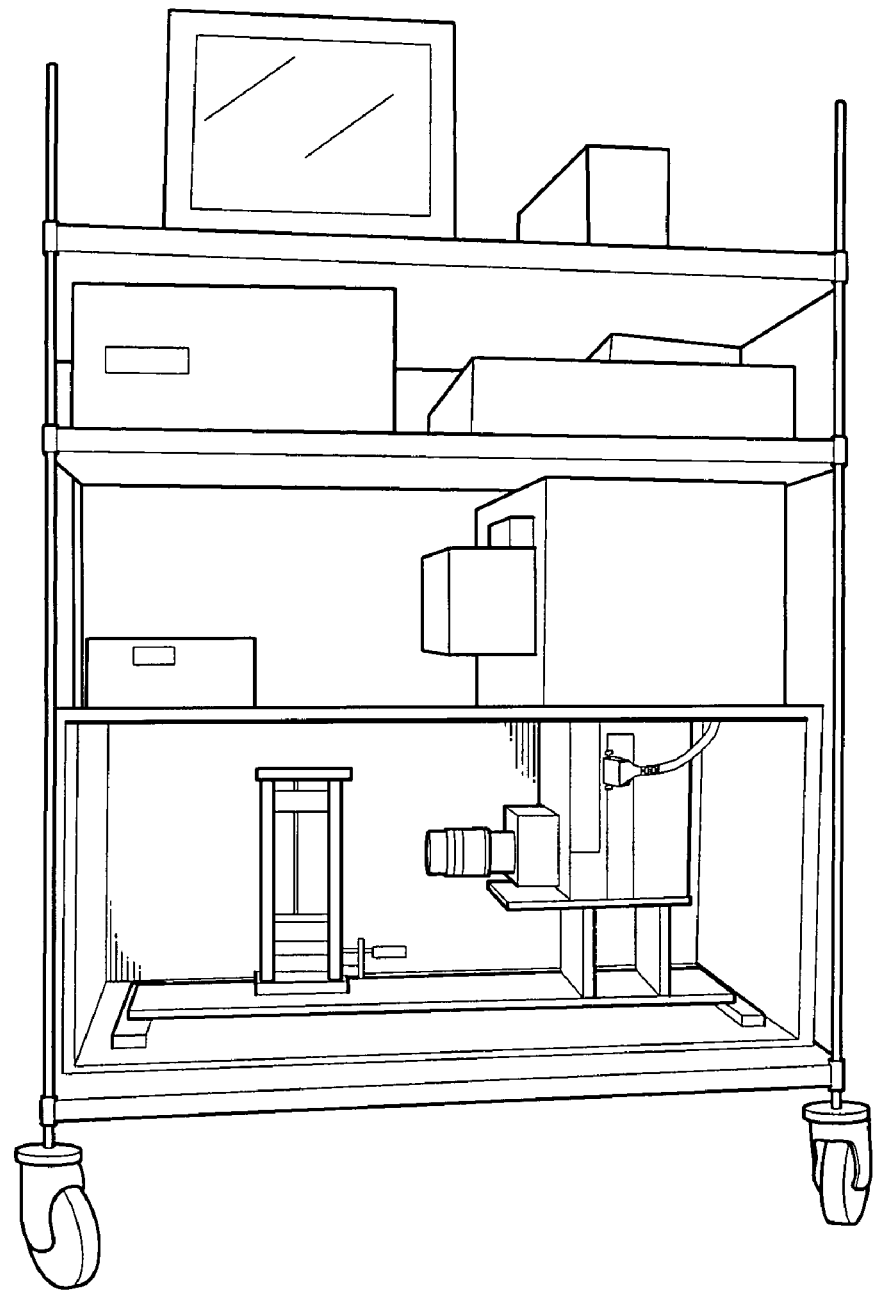
FIG. 2 depicts an exemplary single source bioluminescent CT scanner. The rotating stage and light sensitive camera is shown on the bottom shelf of the cart. The side of the light tight enclosure has been removed for system visualization.
Figure 3:
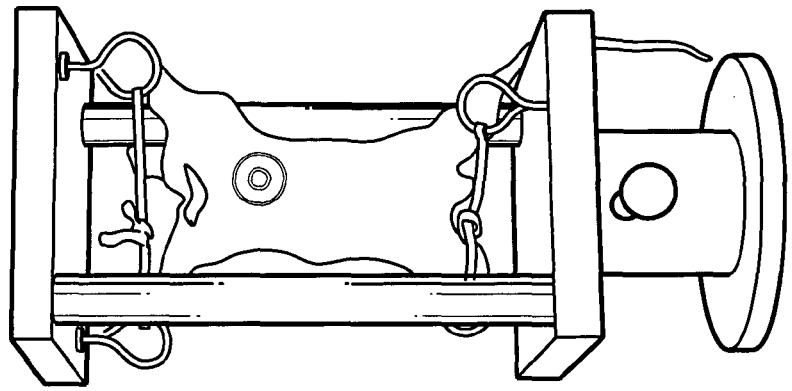
FIG. 3 depicts bioluminescence emitted from the lungs of a mouse following exposure to an adenovirus which has delivered the primary gene and reporter gene (producing luciferase) to the lungs. The emitted light can be seen from multiple angles according to exemplary embodiments. This is a precursor to being able to reconstruct the 3D distribution of the light source (s).
Figure 3:
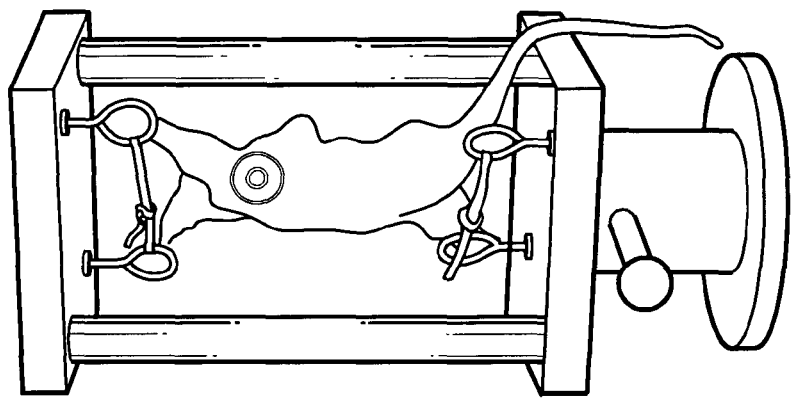
Figure 3:
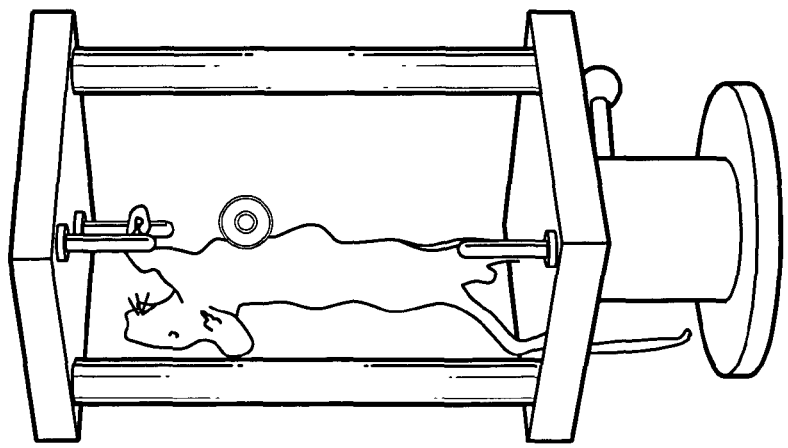
Figure 4:
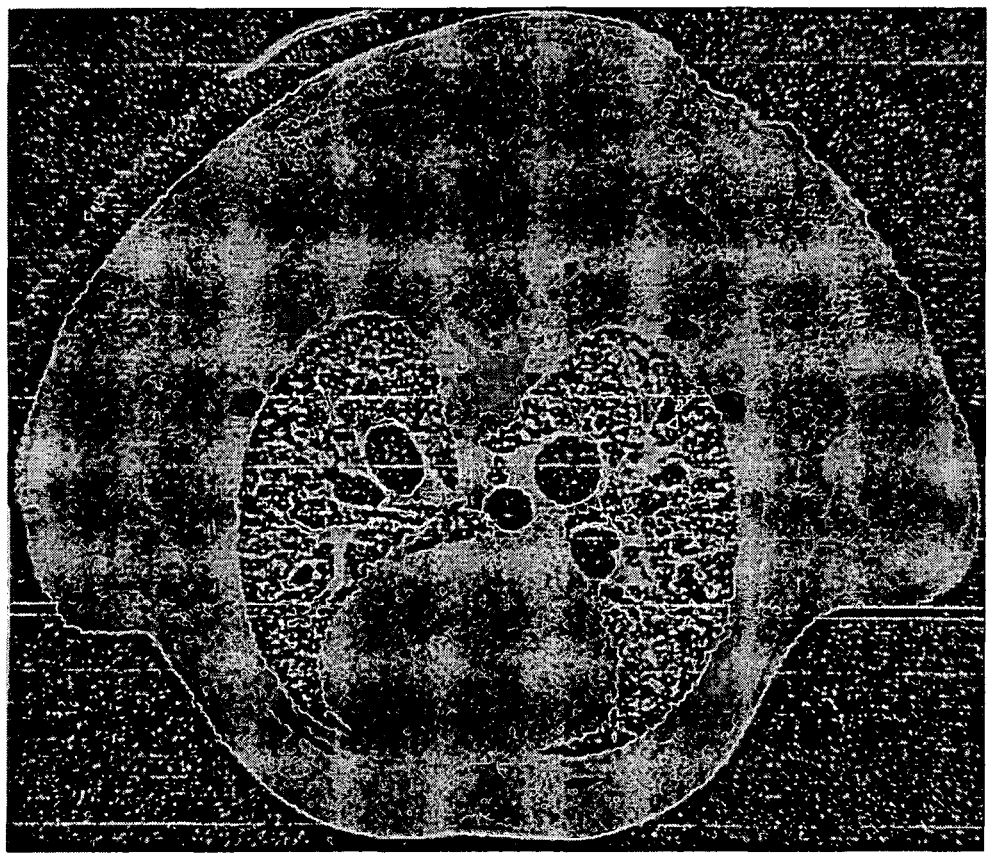
FIG. 4 depicts an exemplary micro-CT image of a lung showing structural components of the mouse thorax with resolution down to the alveolar level. This sort of anatomic image serves to provide the knowledge of the distribution of light scatterers.

One or more exemplary embodiments are now described in detail hereinbelow and in the attachments hereto. Referring to the drawings, like numbers indicate like parts throughout the views. As used in the description herein and attachments hereto, the meaning of "a," "an," and "the" includes plural reference unless the context clearly dictates otherwise. Also, as used in the description herein and attachments hereto, the meaning of "in" includes "in" and "on" unless the context clearly dictates otherwise. Finally, as used in the description herein and attachments hereto, the meanings of "and" and "or" include both the conjunctive and disjunctive and may be used interchangeably unless the context clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The present invention relates to systems and methods for detecting a light-emitting source distribution as well as systems and methods for reconstructing an image from the detected light signals and tomographic images obtained from one or more other modalities, such as an image volume from CT or micro-CT. Some embodiments may include one or more cameras arranged, e.g., symmetrically, on a spherical surface to detect a light emitting source distribution in three dimensions. Alternative embodiments may include asymmetrical camera arrangements and/or other three-dimensional surface arrangements. In some embodiments, other optical mechanisms can be used to intercept and direct signals to the cameras including, but not limited to, mirror and/or fiber systems.

Some further embodiments may detect and record bioluminescent emissions and/or fluorescent emissions. This image data, along with associated x-ray CT images of the same object, can be used to reconstruct a three-dimensional emission image volume and register the bioluminescent CT image to a corresponding x-ray CT or micro-CT image volume of anatomical and pathological structures. In some such embodiments, the bioluminescent (or fluorescent) reconstruction process can be enhanced through the use of knowledge gained from x-ray CT or other anatomic information gathered by use of other imaging devices including, but not limited to, MRI or ultrasound. As a non-limiting example, emitted photons can be collected from multiple directions in three dimensions with respect to a living animal or any other light emitting structure of interest marked by bioluminescent reporter luciferases or fluorescent sources. In some embodiments, a lung and/or various tumors may be imaged.

According to exemplary embodiments, optical properties of an object are presumed to be already known, and the photon-emitting source distribution may be computed based on these known optical properties. Therefore, the imaging models for the systems and methods according to exemplary embodiments are approximately linear, while that for the conventional techniques, such as diffuse CT, are nonlinear and correspondingly more difficult to solve.

By combining a system for detecting light emission from multiple angles of view simultaneously or sequentially with an imaging modality which allows the evaluation of two and three dimensional structural information, such as micro x-ray CT, the anatomic and/or structural details gained from the micro x-ray CT can be used to estimate the distribution of light scattering structures for purposes of directing the computed tomographic calculations required to create BLCT cross-sectional or volumetric images. Such a system may enable, as non-limiting examples, both the calculation of the computed tomograms of chemo-luminescence and the linking of the computed tomograms of chemo-luminescence to the highly detailed anatomic image sets derived from the x-ray CT imaging. In some embodiments, the tomographic reconstruction of bioluminescence can provide important added detail regarding regional location of reporter gene activity. By knowing the location of reporter gene activity and having micro-resolution images of anatomy, a user can follow the link between gene activation and pathologic processes.

Typical Storage and Processing Architecture

In one exemplary embodiment, the imaging and reconstruction system includes a system processor potentially including multiple processing elements. The term processing element may refer to (1) a process running on a particular piece, or across particular pieces, of processing hardware, (2) a particular piece of processing hardware, or either (1) or (2) as the context allows. Each processing element can be supported via a standard general purpose processor such as an Intel-compatible processor platforms preferably using at least one CELERON, PENTIUM, XEON, ITANIUM (Intel Corp., Santa Clara, Calif.) class processor; alternative processors such as MIPS (MIPS Technologies, Mountain View, Calif.) or UltraSPARC (Sun Microsystems, Palo Alto, Calif.) could be used in other embodiments. The system processor, or the one or more processing elements thereof, can include one or more field programmable gate arrays (FPGAs), programmable digital signal processors (DSPs) and/or application specific integrated circuits (ASICs) configured to perform at least a portion of the functionality according to the present invention. In other embodiments, an embedded microprocessor can be used such as, but not limited to, an ARM (ARM, Carlsbad, Calif.) processor core.

In some embodiments, the system processor can include a combination of general purpose processors, ASICs, DSPs and/or FPGAs. In some embodiments, the systems and methods of the present invention, as described above, can be distributed across multiple processing elements. In some such embodiments, aspects of the functionality or portions thereof may be executed in series or in parallel; particular functionality or portions thereof executed a multiplicity of times may also occur in series or parallel.

In a system processor including at least one general purpose processor, the general purpose processor typically runs an appropriate operating system such as WINDOWS/NT, WINDOWS 2000 or WINDOWS/XP (Microsoft, Redmond, Wash.), IRIX (Silicon Graphics, Mountain View, Calif.), SOLARIS (Sun Microsystems, Palo Alto, Calif.), or LINUX (or other UNIX variant). In one embodiment, the Windows 2000 operating system is used.

The SDS may include a variety of primary and secondary storage elements. In one embodiment, the SDS can include random access memory (RAM) as part of the primary storage; the amount of RAM might range from 512 MB to 4 GB in some embodiments. The primary storage can, in some embodiments, include other forms of memory such as cache memory, registers, non-volatile memory (e.g., FLASH, ROM, EPROM, etc.), etc.

The SDS can also include secondary storage including single, multiple and/or varied servers and storage elements. For example, the SDS can use internal storage devices connected to the system processor. In embodiments where a single processing element supports all of the system functionality, a local hard disk drive can serve as the secondary storage of the SDS, and a disk operating system executing on such a single processing element can act as a data server receiving and servicing data requests. A system bus can serve as the communication channel between the system processor and the SDS (typically, at least RAM and the hard disk drive).

It will be understood by those skilled in the art that the different information used in the imaging and image reconstruction processes and systems according to the present invention can be logically or physically segregated within a single device serving as secondary storage for the SDS; multiple related data stores accessible through a unified management system, which together serve as the SDS; or multiple independent data stores individually accessible through disparate management systems, which may in some embodiments be collectively viewed as the SDS. The various storage elements that comprise the physical architecture of the SDS may be centrally located or distributed across a variety of diverse locations.

The architecture of the secondary storage of the system data store may vary significantly in different embodiments. In several embodiments, database(s) are used to store and manipulate the data; in some such embodiments, one or more relational database management systems, such as DB2 (IBM, White Plains, N.Y.), SQL Server (Microsoft, Redmond, Wash.), ACCESS (Microsoft, Redmond, Wash.), ORACLE (Oracle Corp., Redwood Shores, Calif.), Ingres (Computer Associates, Islandia, N.Y.), MySQL (MySQL AB, Sweden) or Adaptive Server Enterprise (Sybase Inc., Emeryville, Calif.), may be used in connection with a variety of storage devices/file servers that may include one or more standard magnetic and/or optical disk drives using any appropriate interface including, without limitation, ATA, IDE and SCSI. In some embodiments, a tape library such as available from Exabyte Corporation (Boulder, Colo.), a storage attached network (SAN) solution such as available from EMC, Inc. (Hopkinton, Mass.), a network attached storage (NAS) solution such as available from Network Appliances (Sunnyvale, Calif.), or combinations thereof may be used. In other embodiments, the data store may use database systems with other architectures such as object-oriented, spatial, object-relational or hierarchical.

Instead of, or in addition to, those organization approaches discussed above, certain embodiments may use other storage implementations such as hash tables or flat files or combinations of such architectures. Such alternative approaches may use data servers other than database management systems such as a hash table look-up server, procedure and/or process and/or a flat file retrieval server, procedure and/or process. Further, the SDS may use a combination of any of such approaches in organizing its secondary storage architecture.

The SDS communicates with the system processor by one or more communication channels. Multiple channels can be involved in some embodiments for supporting communication between processing elements of the system processor and portions of the SDS. Such channels can include without limitation computer network, direct dial-up connection, dedicated connection, direct or indirect connection such as via a bus connection, parallel or serial connection, USB connection, null modem connection or wireless connection utilizing an appropriate communication protocol such as BLUETOOTH, IRDA, 802.11b or other suitable channel as would be known to those skilled in the art.

All forms of data, including raw, intermediate, and computed can be stored on one or more SDS either temporarily or permanently. In particular, the SDS can store, without limitation, image data, including volumetric image data, reconstruction intermediate data, final reconstructed imaging data, imaging parameters, and reconstruction parameters. Further, the SDS may, in some embodiments, store instructions for performing the various imaging and reconstruction tasks, or portions of such tasks.

Light Sensitive Cameras

In one embodiment, ten CCD cameras can be arranged at the center of each identical face of a dodecahedron, except for the two facing the front and back ends of an object to be imaged. Each of the 10 cameras can point to the iso-center where the object can be fixed on a holder. The imaging geometry can be implemented by a structure holding each camera in its fixed position. Data from the cameras can be transmitted to one or more processing elements for further processing and image reconstruction. A light-free housing can be used to house the imaging cameras. Once the frame of the imaging device is arranged, a camera can be mounted at any spot of the 12 nominal positions on the dodecahedron. One or more cameras can be geometrically and photographically calibrated with reference phantoms. An optical surface scanner can be combined with the imaging frame for the registration purpose.

One skilled in the art will recognize that other arrangements of cameras are possible, including geometrically symmetrical and asymmetrical configurations, with or without appropriate optical paths such as obtained through use of mirrors or fiberoptic relay paths. In some embodiments, one or more cameras can be rotated around an object of interest. Alternatively, or in combination, the subject of the imaging can be rotated on one or more axis. As a non-limiting example, such embodiments can be used in cases where light emission is unstable. In this case, dynamic bioluminescent and/or fluorescent tomographic imaging would be feasible.

In one embodiment, one or more cooled back-thinned integrating CCD cameras can be used for imaging. The camera package can include a 2.2 L or other appropriately sized end-on liquid nitrogen dewar for cooling. Alternatively, an omni-directional dewar can be used to allow cameras to be mounted in any orientation while keeping the dewar right-side up. In some embodiments, the imagers can be sensitive to one or more bioluminescent sources of different spectral characteristics. Other types of light sensitive cameras can also be used. Analog films can be used with appropriate manipulations.

A living organism, or other structure of interest, can be scanned using a multi-detector spiral CT, another appropriate method of imaging known to one skilled in the art, or a micro x-ray CT scanner. From this imaging, a distribution of optical properties of the object can be derived to guide associated bioluminescent and/or fluorescent tomographic imaging.

Camera Control

According to exemplary embodiments, one or more camera control elements may be used. A camera control element can include one or more processing elements and can be in communication with the SDS. The imaging cameras of the present invention can be in communication with the one or more camera control elements. Camera control elements can perform digitization of output from cameras and other processing as appropriate. Relevant imaging parameters can be controlled by the camera control elements. As non-limiting examples, imaging parameters such as focus, exposure time, aperture, can be configured. Additional parameters known to one skilled in the art can also be configured as appropriate.

In some embodiments, all cameras can be controlled by a single controller element. In other embodiments, a single controller element may be used to control multiple cameras. In such an embodiment, cameras may be arbitrarily grouped into arrays and each array can be controlled by a single controller element. Each camera acquisition chain can then operate independently. Still further embodiments can include a master controller element to provide control and synchronization for an entire camera array. In one embodiment, one camera is controlled by a single controller element. One skilled in the art will recognize that other configurations of cameras and controller elements are possible.

Some embodiments can include one or more hierarchies of control elements and/or processing elements. Different levels of hierarchy can perform the same or different functions. In one embodiment, images from low-level camera control elements are passed to higher level processing elements and/or control elements for additional processing and/or image reconstruction, as further described below. Control elements and processing elements can be communicatively coupled via any suitable communication means including computer network, wired or wireless direct link, bus connection and as further described below.

In one embodiment, individual cameras can be controlled with an external camera control element in communication with a PCI controller card in communication with one or more processing elements. The PCI controller card and the camera control element can be communicatively coupled via an RS-422 link or other suitable serial or parallel connection. The external camera control element and the camera can be communicatively coupled via a parallel interface. In one such embodiment, cameras output analog signals which are digitized by one or more external camera control elements. To minimize noise, the length of the link between the camera and the controller box can be minimized.

In one embodiment, the light-emitting source data acquisition process can include one or more of the following steps: (1) reset and/or initialize cameras; (2) execute a programmable, configurable, or manual shutter open on one or more cameras; (3) execute a programmable, configurable, or manual shutter close on one or more cameras; (4) transfer image data to one or more camera control elements, processing element, or SDS; and (5) store the images in the SDS. Additional embodiments can have shutter times configured to occur simultaneously across multiple cameras and/or automatically after a predetermined time delay.

Image Reconstruction Using an Iterative Method or Other Methods

Given the ill-posed nature of the imaging and sampling geometry, an iterative image reconstruction approach may be used utilizing prior knowledge on the distribution to be reconstructed. The iterative approach can be used in the case of incomplete and/or noisy data. Also, the iterative approach easily accommodates prior knowledge and imaging physics.

An interface from one or more camera control elements and/or processing elements to one or more reconstruction engines can be provided. The systems of the present invention can acquire optical properties of the object being imaged and then compute the light-emitting source distribution based on the optical properties. Therefore, the imaging model is approximately linear. In one embodiment, x-ray CT data is used to regularize the BLCT reconstruction problem and transform it from a nonlinear one to linear one and thereby greatly simplify it.

Even with attenuation and scattering taken into account based on a CT or micro-CT image volume, a discrete BLCT imaging model can still be linearly expressed as $Ax=b$, where the observed data $b=(b^1, \ldots, b^M) \in R^M$, original emitting source distribution $x=(x_1, \ldots, x_N) \in R^N$, and a known non-zero $M \times N$ matrix $A=(A_{ij})$. The coefficients of the matrix A depend on the anatomical structures and their optical properties according to the classic Radiative Transfer Equation (using the Monte Carlo method) or the well-known diffusion approximation or another appropriate method. The systems and methods according to exemplary embodiments can reconstruct the image x from the data b.

A generalized BLCT algorithm according to one embodiment can include one or more of the following steps: (1) reconstruction and segmentation of an x-ray CT image volume, (2) association of optical properties to each segmented region in the x-ray CT volume based on a library of optical properties, (3) determination of coefficients of the forward imaging matrix $A=(A_{ij})$ based, e.g., on Monte Carlo simulations, (4) reconstruction of the emitting source distribution x by inverting the matrix A, subject to the constraints imposed by the segmented anatomical structures, their properties, and known features of the underlying source distribution (such as the homogeneity or parametric form of the source distribution, the shape or intensity of the source). According to exemplary embodiments, bioluminescent emissions, and well as other light-emitting source distributions, such as fluorescent source distributions, may be detected and reconstructed in this way or another alternative way.

As non-limiting examples, the optical properties of step two can include absorption coefficients, scattering coefficients, scattering anisotropy, indices of refraction, and other appropriate parameters known to one skilled in the art. Monte Carlo simulations can be used to predict bioluminescent signals and construct the matrix A based on the CT/micro-CT image volume of the object. Other methods, such as finite element methods and meshfree methods, may be also used for this purpose. After image segmentation, optical properties can be assigned to each segment based on a library of optical properties.

In one embodiment, both the ordered-subset expectation maximization (OS-EM) and the ordered-subset version of the simultaneous algebraic reconstruction technique (OS-SART) schemes for BLCT can be implemented. A roughness penalty method for BLCT or other method known to one skilled in the art can also be used.

Although an iterative method may be most suitable to the image reconstruction task in one embodiment, other image reconstruction methods can be used. Even further, the iterative procedure described above is only an example, and should not be interpreted as a limiting description.

As far as image reconstruction methods are concerned, it is emphasized that there are multiple options or possibilities. In addition to an iterative reconstruction strategy as described above, numerical solutions to the Radiative Transfer Equation or its approximation, such as the diffusion equation, can be useful as well. A fast analytic method would be very useful in practice. In one embodiment, an analytic approach known as the Kirchhoff approximation may be adapted for bioluminescent tomography of diffuse media with an embedded source distribution. Other numerical methods, such as finite element methods and/or meshfree methods, are also feasible for the same purpose.

CT/Micro-CT Scanner

Any state-of-the-art micro-CT scanner can be used according to exemplary embodiments. In some embodiments, the ImTek MicroCAT II or the SkyScan-1076 in-vivo micro-CT system can be used.

In other embodiments, the data acquisition system can include one or more of the following items: a dedicated embedded data acquisition and control computer, two 130 kVp ultra-high resolution µfocus X-ray systems, two 100/50 mm dual-field image intensifiers, and two 2048×2048 CCD cameras. The scanner can include one or more processing elements in communication with the SDS, a multi-axis precision scanner and specimen manipulator with linear servo drives, remotely configurable motorized source-detector geometries, a signal and power slip ring for continuous rotation, and a means to move data between acquisition and processing. The slip ring can have two independent capacitively coupled data transmission channels with full-duplex fibre channel interfaces. The one or more processing elements, the slip ring data channels and the SDS can be communicatively coupled. In one embodiment, they can be connected via one or more fiber optic cables.

One embodiment may be built on an optical grade table for vibration isolation and precision alignment. An imaging chain of source arrays, detector arrays, and accessories, alone or in combination, can be mounted on a rotating plate which is in turn supported by an open bearing and rigid stand. The axis of rotation can set to any appropriate angle including vertical and horizontal. The geometry of each imaging chain can be individually configured to suit a wide variety of operating modes. Each x-ray tube and image intensifier can be moved radially, while each image intensifier can also be moved laterally. The object can rest horizontally in a holder mounted to a linear axis with a certain amount of axial travel room for slice positioning. One exemplary embodiment is capable of achieving spatial resolution of 100 lp/mm for excised samples, and temporal resolution of 1.8 seconds for objects up to 120 mm in diameter. The system can be configured to allow a wide range of intermediate combinations of scan time and spatial resolution.

System Integration

The light-emitting source distribution CT device and the anatomic imaging scanner, such as a micro x-ray CT scanner, can be electronically and mechanically integrated but need not be in all embodiments. In one embodiment, the hardware structures of the two imaging units can share a table and/or a holder attached to a table. This embodiment can allow the translation of an object for x-ray CT scanning to be extended into the light-emitting CT device in a precise and/or repeatable fashion. Some embodiments may be configured to optimize and integrate software packages for Monte Carlo simulation (another kind of simulation, such as that based on finite element computation), CT and/or micro-CT data preprocessing and reconstruction, BLCT reconstruction, image visualization and analysis. A user interface to perform and/or to configure such functions can also be provided in some embodiments; in some such embodiments, the user interface can further allow viewing of results and may allow control of parameters with respect to such viewing. Any software capable of performing such functions can be implemented on one or more processing elements.

Exemplary Applications

The following applications are intended as illustrative examples only and are not limiting of the invention. According to exemplary embodiments, advanced imaging, such as lung imaging, is enabled in that the structural and function information can be obtained concurrently at the molecular level, and can be evaluated on a regional, sub-lobar basis. This combination allows simultaneous examination of gene expression and anatomic structures and improves understanding of the human lungs.

Exemplary embodiments may be used in gene therapy imaging, to probe the distribution of the administered gene, reporter genes, such as those producing luciferase, can be included in the transfecting virus. These genes cause the emission of light, enabling the functional gene to be identified within the target tissue.

Exemplary embodiments may also be useful in evaluating transgene expression in the lung; gene transfer vectors; gene transfer to the respiratory epithelium of mice; in vivo bioluminescence imaging; understanding the site of transgene expression in the lung; human lung lobe imaging and sheep-based emphysema model evaluation; understanding the site of gene therapy, and its consequences; and understanding the pathophysiology of airway vs. alveolar infection.

The embodiments described above are given as illustrative examples only. It will be readily appreciated by those skilled in the art that many deviations and other applications may be made from the specific embodiments disclosed in this specification without departing from the scope of the invention.

What is claimed is:

1. A method, comprising:
   imaging an object using a tomographic imaging device to produce a reconstructed image;
   mapping optical absorption properties and scattering properties of the object to the reconstructed image, resulting in mapped optical properties;
   detecting internally derived bioluminescent signals emitted from the object using a bioluminescent imaging device, wherein the internally derived bioluminescent signals are not reliant on external energy excitation; and
   reconstructing a bioluminescent source distribution of the object from the internally derived bioluminescent signals based at least on the mapped optical properties, wherein the reconstructing step comprises generating an imaging matrix of coefficients dependent on the mapped optical properties and an anatomical structure of the object by solving a radiative transfer equation or an approximation to the radiative transfer equation via at least one of a finite-element method, a mesh-free method, or a Monte Carlo simulation.

2. The method of claim 1, further comprising supplying, via the reconstructed image, two-dimensional or three-dimensional structural details of the object.

3. The method of claim 1, further comprising supplying, via the bioluminescent source distribution, two-dimensional or three-dimensional distribution of light emission from the object.

4. The method of claim 1, wherein the step of reconstructing further comprises reconstructing the bioluminescent source distribution to represent multiple types of source distributions with various spectral characteristics.

5. The method of claim 1, wherein the step of reconstructing further comprises reconstructing the bioluminescent source distribution from a single angle of view or multiple angles of view.

6. The method of claim 1, wherein the step of reconstructing further comprises reconstructing the bioluminescent source distribution by using an iterative approach or an analytic approach.

7. The method of claim 1, wherein the step of detecting optical signals further comprises utilizing optical path components for one or more paths.

8. The method of claim 1, supplying, via the bioluminescent source distribution, quantitative features of underlying source distributions of the object.

9. The method of claim 1, wherein the optical absorption properties and the scattering properties of the object comprise at least one of absorption coefficients, scattering coefficients, scattering anisotropy, indices of refraction, and features of underlying sources.

10. The method of claim 1, wherein the imaging step comprises configuring a tomographic imaging modality, wherein the tomographic imaging modality includes at least one of x-ray computed tomography, magnetic resonance imaging, or ultrasound.

11. The method of claim 1, further comprising segmenting the reconstructed image into at least one region, wherein the step of mapping maps the optical absorption properties and the scattering properties of the object to the at least one region of the image.

12. The method of claim 1, further comprising registering the reconstructed image with the bioluminescent signals before producing the bioluminescent source distribution.

13. The method of claim 12, wherein the step of registering comprises registering the reconstructed image with the bioluminescent signal by using a landmark-based method, a landmark free method, or an optical surface imager method.

14. A system, comprising:
   a tomographic imaging device for imaging an object to produce a reconstructed image;
   a library of optical absorption properties and scattering properties of the object, based at least on available data;
   a processor for mapping the optical absorption properties and scattering properties of the object to the reconstructed image, resulting in mapped optical properties; and
   a bioluminescent imaging device comprising one or more imagers sensitive to one or more internally derived bioluminescent sources of spectral characteristics, wherein the internally derived bioluminescent signals are not reliant on external energy excitation, and wherein the bioluminescent imaging device is configured for
      detecting internally derived bioluminescent signals emitted from the object by using the one or more imagers, and
      reconstructing a bioluminescent source distribution of the object based at least on the mapped optical properties, wherein the bioluminescent source distribution is produced using a radiative transfer equation or an approximation to the radiative transfer equation.

15. The system of claim 14, wherein the reconstructed image conveys two-dimensional structural details or three-dimensional structural details of the object.

16. The system of claim 14, wherein the bioluminescent source distribution conveys two-dimensional distribution or three-dimensional distribution of light emission from the object.

17. The system of claim 14, wherein the bioluminescent source distribution is reconstructed to represent multiple types of source distributions with at least one spectral characteristics.

18. The system of claim 14, wherein the bioluminescent source distribution is reconstructed from a single angle of view or multiple angles of view.

19. The system of claim 14, wherein the bioluminescent source distribution is reconstructed using an iterative approach or an analytic approach.

20. The system of claim 14, wherein the bioluminescent imaging device utilizes sensors for detecting emission of optical signal.

21. The system of claim 20, wherein the bioluminescent imaging device further comprises optical path components.

22. The system of claim 14, wherein the bioluminescent source distribution conveys quantitative features of at least one underlying source distribution.

23. The system of claim 14, wherein the optical properties include at least one of absorption coefficients, scattering coefficients, scattering anisotropy, indices of refraction, and features of underlying bioluminescence sources.

24. The system of claim 14, wherein the tomographic imaging device enables a tomographic imaging modality comprising at least one of x-ray computed tomography scanning, micro computed tomography scanning, magnetic resonance imaging, micro magnetic resonance imaging, or ultrasound imaging.

25. The system of claim 14, wherein the processor segments the reconstructed image into at least one region and maps the optical absorption properties and the scattering properties of the object to the at least one region.

26. The system of claim 14, wherein the processor registers the reconstructed image with the bioluminescent signals before the bioluminescent source distribution is produced.

27. The system of claim 26, wherein the processor registers the reconstructed image with the bioluminescent signals by using a landmark-based method, a landmark-free method, or an optical surface imager based method.

* * * * *